(12) United States Patent
Fetzer et al.

(10) Patent No.: US 9,746,447 B2
(45) Date of Patent: Aug. 29, 2017

(54) APPARATUSES, SYSTEMS, AND METHODS FOR INSPECTING A COMPONENT

(71) Applicant: The Boeing Company, Chicago, IL (US)

(72) Inventors: Barry A. Fetzer, Renton, WA (US); Christopher R. Brown, Seattle, WA (US); Dennis P. Sarr, Kent, WA (US); Michael J. Duncan, Lake Tapps, WA (US)

(73) Assignee: The Boeing Company, Chicago, IL (US)

( * ) Notice: Subject to any disclaimer, the term of this patent is extended or adjusted under 35 U.S.C. 154(b) by 298 days.

(21) Appl. No.: 14/529,114

(22) Filed: Oct. 30, 2014

(65) Prior Publication Data

US 2016/0123934 A1   May 5, 2016

(51) Int. Cl.
*G01N 29/04* (2006.01)
*G01N 29/22* (2006.01)
(Continued)

(52) U.S. Cl.
CPC ......... *G01N 29/265* (2013.01); *G01N 29/043* (2013.01); *G01N 29/225* (2013.01);
(Continued)

(58) Field of Classification Search
CPC ...... G01N 29/265; G01N 29/24; G01N 29/04; G01N 2291/0289; G01N 2291/023; G01N 2291/10; G01N 2291/263
(Continued)

(56) References Cited

U.S. PATENT DOCUMENTS 4,472,975 A   9/1984   Beck et al.
5,469,744 A   11/1995  Patton et al.
(Continued)

FOREIGN PATENT DOCUMENTS

DE   3719105   12/1988
EP   1625676   4/2013
(Continued)

OTHER PUBLICATIONS

European Search Report for EP Application No. 15192433.9 dated Apr. 14, 2016.
(Continued)

*Primary Examiner* — J M Saint Surin
(74) *Attorney, Agent, or Firm* — Kunzler Law Group, PC

(57) ABSTRACT

Described herein is an apparatus for inspecting a component includes a first feature inspector with at least one wave transducer configured to inspect a first feature of the component. The first feature inspector further includes at least one displacement sensor configured to detect a displacement of the at least one wave transducer of the first feature inspector relative to the first feature of the component. The apparatus further includes a second feature inspector with at least one wave transducer configured to inspect a second feature of the component. The second feature inspector further includes at least one displacement sensor configured to detect a displacement of the at least one wave transducer of the second feature inspector relative to the second feature of the component.

21 Claims, 8 Drawing Sheets

(51) Int. Cl.
*G01N 29/28* (2006.01)
*G01N 29/265* (2006.01)

(52) U.S. Cl.
CPC ....... *G01N 29/28* (2013.01); *G01N 2291/044* (2013.01); *G01N 2291/105* (2013.01); *G01N 2291/2638* (2013.01)

(58) Field of Classification Search
USPC .......................................................... 73/625
See application file for complete search history.

(56) References Cited

U.S. PATENT DOCUMENTS

| | | | |
|---|---|---|---|
| 5,814,731 A | | 9/1998 | Alexander et al. |
| 5,984,415 A | | 11/1999 | Schumacher et al. |
| 5,986,762 A | * | 11/1999 | Challener .......... G01N 21/7743 356/403 |
| 6,344,656 B1 | * | 2/2002 | Hopkins .............. G01B 11/005 250/559.22 |
| 6,481,290 B1 | | 11/2002 | MacInnis et al. |
| 6,658,939 B2 | | 12/2003 | Georgeson et al. |
| 6,733,457 B2 | | 5/2004 | Flesch et al. |
| 6,948,369 B2 | | 9/2005 | Fleming et al. |
| 7,034,271 B1 | * | 4/2006 | Sinclair .................. G02B 21/18 250/201.3 |
| 7,249,512 B2 | | 7/2007 | Kennedy et al. |
| 7,263,889 B2 | | 9/2007 | Kennedy et al. |
| 7,617,732 B2 | | 11/2009 | Bui et al. |
| 7,640,810 B2 | | 1/2010 | Kennedy et al. |
| 7,640,811 B2 | | 1/2010 | Kennedy et al. |
| 7,643,893 B2 | | 1/2010 | Troy et al. |
| 7,644,618 B2 | | 1/2010 | Fetzer et al. |
| 7,690,259 B2 | | 4/2010 | Bui et al. |
| 7,743,660 B2 | | 6/2010 | Marsh et al. |
| 7,784,348 B2 | | 8/2010 | Dubois et al. |
| 7,836,768 B2 | | 11/2010 | Young et al. |
| 7,859,655 B2 | | 12/2010 | Troy et al. |
| 8,082,793 B2 | | 12/2011 | Sarr et al. |
| 8,087,298 B1 | | 1/2012 | DiMambro et al. |
| 8,128,027 B2 | | 3/2012 | Lee |
| 8,438,928 B2 | | 5/2013 | Frederick et al. |
| 8,459,120 B2 | | 6/2013 | Keeton et al. |
| 8,650,959 B2 | | 2/2014 | De Odorico et al. |
| 8,892,252 B1 | | 11/2014 | Troy et al. |
| 9,126,676 B2 | | 9/2015 | DeCraene et al. |
| 9,127,971 B2 | * | 9/2015 | Sarr ...................... G01N 29/041 |
| 9,316,619 B2 | | 4/2016 | Lombardo et al. |
| 9,354,206 B2 | | 5/2016 | Zalameda et al. |
| 9,372,173 B2 | | 6/2016 | Thomson et al. |
| 2006/0243051 A1 | * | 11/2006 | Bui ...................... G01N 29/043 73/618 |
| 2010/0224001 A1 | | 9/2010 | Brignac |
| 2012/0025031 A1 | | 2/2012 | Stachniak et al. |
| 2012/0097800 A1 | | 4/2012 | Burroughs et al. |
| 2012/0160967 A1 | | 6/2012 | Scott et al. |
| 2013/0105634 A1 | | 5/2013 | DeCraene et al. |
| 2013/0145850 A1 | | 6/2013 | Lute, Jr. et al. |
| 2013/0209256 A1 | | 8/2013 | Yates et al. |
| 2014/0305216 A1 | | 10/2014 | Hafenrichter et al. |
| 2014/0373608 A1 | * | 12/2014 | Bellemare ................ G01N 3/46 73/82 |
| 2014/0376768 A1 | | 12/2014 | Troy et al. |
| 2015/0053015 A1 | | 2/2015 | Sarr et al. |
| 2015/0329221 A1 | | 11/2015 | Georgeson et al. |
| 2016/0123933 A1 | | 5/2016 | Fetzer et al. |

FOREIGN PATENT DOCUMENTS

| | | |
|---|---|---|
| JP | 2013088242 | 5/2013 |
| WO | 2005/032003 | 4/2005 |
| WO | 2013/070840 | 5/2013 |

OTHER PUBLICATIONS

Sanz, et al., Robotized Inspection System of the External Aircraft Fuselage based on Ultrasound, The 2010 IEEE/RSJ International Conference on Intelligent Robots and Systems, Oct. 18-22, 2010, Taipei, Taiwan.

Notice of Allowance for U.S. Appl. No. 14/528,897 dated Jan. 18, 2017.

* cited by examiner

APPARATUSES, SYSTEMS, AND METHODS FOR INSPECTING A COMPONENT

FIELD

This disclosure relates generally to the inspection of components for detecting defects in the components, and more particularly to maintaining a probe at a desired position relative to components during inspection of the components.

BACKGROUND

Some techniques for non-destructively inspecting components include the transmission of acoustic waves through the components. The acoustic waves are generated by wave transducers that are desirably positioned normal to the surface of the component being inspected. The wave transducers are moved along the surface as they transmit acoustic waves into and receive reflected acoustic waves from the component. Often, the movement of the wave transducers along the surface is controlled according to a predetermined model of the component, or predetermined teach paths, obtained prior to inspection.

SUMMARY

The subject matter of the present application has been developed in response to the present state of the art, and in particular, in response to the problems associated with the inspection of components that have not yet been fully solved by currently available techniques. For example, current techniques fail to compensate for the inadvertent pitch and/or roll of a component being inspected. A component being tested can be fixed in place by a fixture. Often, the fixture tends to introduce an inadvertent pitch and/or roll of the component. Additionally, the actual, or as-built, configuration of a component being tested may be different than the predetermined, or theoretical, model of the component. The pitch and roll of a component by a fixture, and differences between the actual configuration and the predetermined model of a component, may introduce inspection errors. The subject matter of the present application has been developed to provide apparatuses, systems, and methods for inspecting components that overcome at least some of the above-discussed shortcomings of prior art techniques.

According to one embodiment, an apparatus for inspecting a component includes a first feature inspector with at least one wave transducer configured to inspect a first feature of the component. The first feature inspector further includes at least one displacement sensor configured to detect a displacement of the at least one wave transducer of the first feature inspector relative to the first feature of the component. The apparatus further includes a second feature inspector with at least one wave transducer configured to inspect a second feature of the component. The second feature inspector further includes at least one displacement sensor configured to detect a displacement of the at least one wave transducer of the second feature inspector relative to the second feature of the component.

In an implementation of the apparatus, the first feature inspector further includes first and second housings spaced longitudinally apart from each other along the first feature. Each of the first and second housings of the first feature inspector houses at least one wave transducer. According to one implementation, the first feature inspector includes a first displacement sensor movably coupled to the first housing of the first feature inspector, and a second displacement sensor movably coupled to the second housing of the first feature inspector.

According to an implementation of the apparatus, the second feature inspector further includes first and second housings spaced laterally apart from each other across the second feature. Each of the first and second housings of the second feature inspector houses at least one wave transducer. In an implementation, the second feature inspector includes a first displacement sensor movably coupled to the first housing of the second feature inspector, and a second displacement sensor movably coupled to the second housing of the second feature inspector.

In one implementation of the apparatus, the first feature includes a cap, and the second feature includes opposing webs angled with respect to the cap.

According to one implementation of the apparatus, displacement of the at least one wave transducer of the first feature inspector relative to the first feature of the component corresponds with a pitch of the component, and displacement of the at least one wave transducer of the second feature inspector relative to the second feature of the component corresponds with a roll of the component.

According to yet one implementation, the apparatus further includes an optical sensor configured to detect changes in a profile of the first and second features of the component. Changes in the profile of the first and second features of the component detected by the optical sensor correspond with at least one of height and lateral changes in the profile of the first and second features of the component.

In another embodiment, a system for inspecting a component includes a probe with a first feature inspector that has at least one wave transducer configured to inspect a first feature of the component. The first feature inspector further includes at least one displacement sensor configured to detect a displacement of the at least one wave transducer of the first feature inspector relative to the first feature of the component. The probe also includes a second feature inspector with at least one wave transducer configured to inspect a second feature of the component. The second feature inspector further includes at least one displacement sensor configured to detect a displacement of the at least one wave transducer of the second feature inspector relative to the second feature of the component. The system also includes an actuator coupled to the probe. The actuator is actuatable to adjust at least one of a linear or angular position of the probe. The system further includes a controller operably coupled to the probe and actuator. The controller is configured to control actuation of the actuator based on at least one of the displacement of the at least one wave transducer of the first feature inspector relative to the first feature of the component or the displacement of the at least one wave transducer of the second feature inspector relative to the second feature of the component.

In one implementation of the system, the controller controls actuation of the actuator to adjust a pitch of the probe based on the displacement of the at least one wave transducer of the first feature inspector relative to the first feature of the component, and to adjust a roll of the probe based on the displacement of the at least one wave transducer of the second feature inspector relative to the second feature of the component.

According to an implementation of the system, the probe further includes at least one optical sensor configured to detect a profile of the first and second features of the component. The controller is further configured to control actuation of the actuator based on changes in the profile of the first and second features of the component detected by the at least one optical sensor.

In one implementation of the system, the controller controls actuation of the actuator to adjust a lateral or height position of the probe based on changes in the profile of the first and second features of the component detected by the at least one optical sensor.

According to an implementation, the controller controls actuation of the actuator to adjust at least one of roll or pitch of the probe based on changes in the profile of the first and second features of the component detected by the at least one optical sensor.

In an implementation of the system, the controller controls actuation of the actuator based solely on one or more of the displacement of the at least one wave transducer of the first feature inspector relative to the first feature of the component, the displacement of the at least one wave transducer of the second feature inspector relative to the second feature of the component, and changes in the profile of the first and second features of the component detected by the at least one optical sensor.

According to one implementation of the system, the controller includes an input module and an output module. The input module is configured to receive signals from the at least one displacement sensor of the first feature inspector and the at least one displacement sensor of the second feature inspector. The output module is configured to convert the signals received from the at least one displacement sensor of the first feature inspector and the at least one displacement sensor of the second feature inspector into actuation commands for actuating the actuator.

In an implementation of the system, the first feature inspector includes at least two wave transducers and at least two displacement sensors each configured to detect a displacement of a respective one of the at least two wave transducers of the first feature inspector. The second feature inspector includes at least two wave transducers and at least two displacement sensors each configured to detect a displacement of a respective one of the at least two wave transducers of the second feature inspector. The input module is configured to aggregate signals received from the at least two displacement sensors of the first feature inspector into a first aggregated signal, and aggregate signals received from the at least two displacement sensors of the second feature inspector into a second aggregated signal. The output module is configured to convert the first aggregated signal into a pitch command for actuating a pitch actuator of the actuator, to convert the second aggregated signal into a roll command for actuating a roll actuator of the actuator.

According to yet another embodiment, a method for inspecting a component includes initiating an inspection of a 3-dimensional structure of the component using at least one wave transducer, detecting displacement of the at least one wave transducer relative to the 3-dimensional structure, and adjusting the position of the at least one wave transducer based on detected displacement of the at least one wave transducer relative to the 3-dimensional structure.

In an implementation, the method further includes determining a pitch of the 3-dimensional structure based on detected displacement of the at least one wave transducer relative to the 3-dimensional structure. Adjusting the position of the at least one wave transducer includes adjusting a pitch of the at least one wave transducer.

In one implementation, the method further includes determining a roll of the 3-dimensional structure based on detected displacement of the at least one wave transducer relative to the 3-dimensional structure. Adjusting the position of the at least one wave transducer comprises adjusting a roll of the at least one wave transducer.

According to yet one implementation, the method further includes detecting a profile of the 3-dimensional structure of the component using at least one optical sensor. The method also includes adjusting a linear position of the at least one wave transducer based on a change in the detected profile of the 3-dimensional structure.

The described features, structures, advantages, and/or characteristics of the subject matter of the present disclosure may be combined in any suitable manner in one or more embodiments and/or implementations. In the following description, numerous specific details are provided to impart a thorough understanding of embodiments of the subject matter of the present disclosure. One skilled in the relevant art will recognize that the subject matter of the present disclosure may be practiced without one or more of the specific features, details, components, materials, and/or methods of a particular embodiment or implementation. In other instances, additional features and advantages may be recognized in certain embodiments and/or implementations that may not be present in all embodiments or implementations. Further, in some instances, well-known structures, materials, or operations are not shown or described in detail to avoid obscuring aspects of the subject matter of the present disclosure. The features and advantages of the subject matter of the present disclosure will become more fully apparent from the following description and appended claims, or may be learned by the practice of the subject matter as set forth hereinafter.

BRIEF DESCRIPTION OF THE DRAWINGS

In order that the advantages of the subject matter may be more readily understood, a more particular description of the subject matter briefly described above will be rendered by reference to specific embodiments that are illustrated in the appended drawings. Understanding that these drawings depict only typical embodiments of the subject matter and are not therefore to be considered to be limiting of its scope, the subject matter will be described and explained with additional specificity and detail through the use of the drawings, in which.

DETAILED DESCRIPTION

Reference throughout this specification to "one embodiment," "an embodiment," or similar language means that a particular feature, structure, or characteristic described in connection with the embodiment is included in at least one embodiment of the present disclosure. Appearances of the phrases "in one embodiment," "in an embodiment," and similar language throughout this specification may, but do not necessarily, all refer to the same embodiment. Similarly, the use of the term "implementation" means an implementation having a particular feature, structure, or characteristic described in connection with one or more embodiments of the present disclosure, however, absent an express correlation to indicate otherwise, an implementation may be associated with one or more embodiments.

Figure 1:
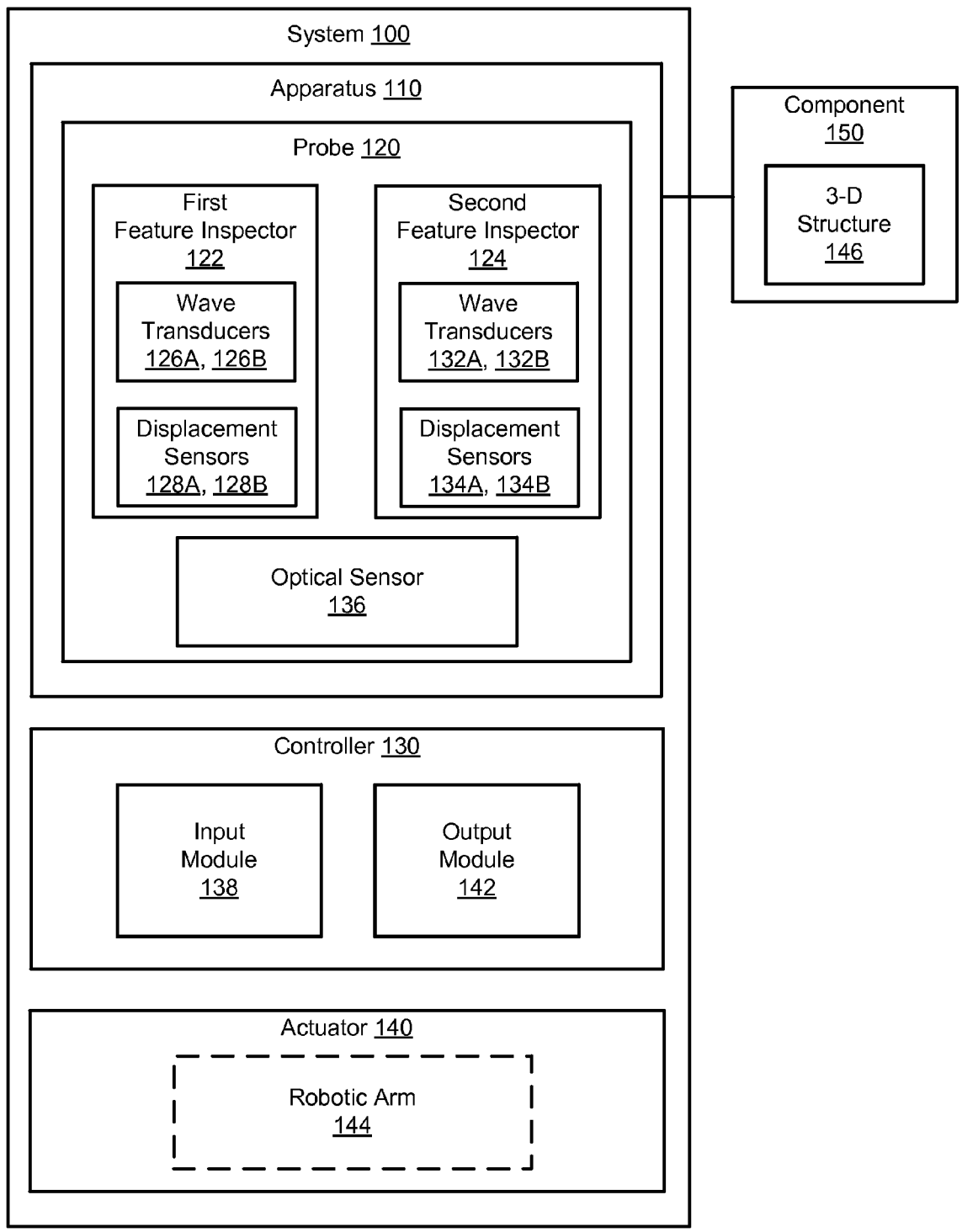
FIG. 1 is a schematic block diagram of a system for inspecting a component according to one embodiment.
Figure 3:
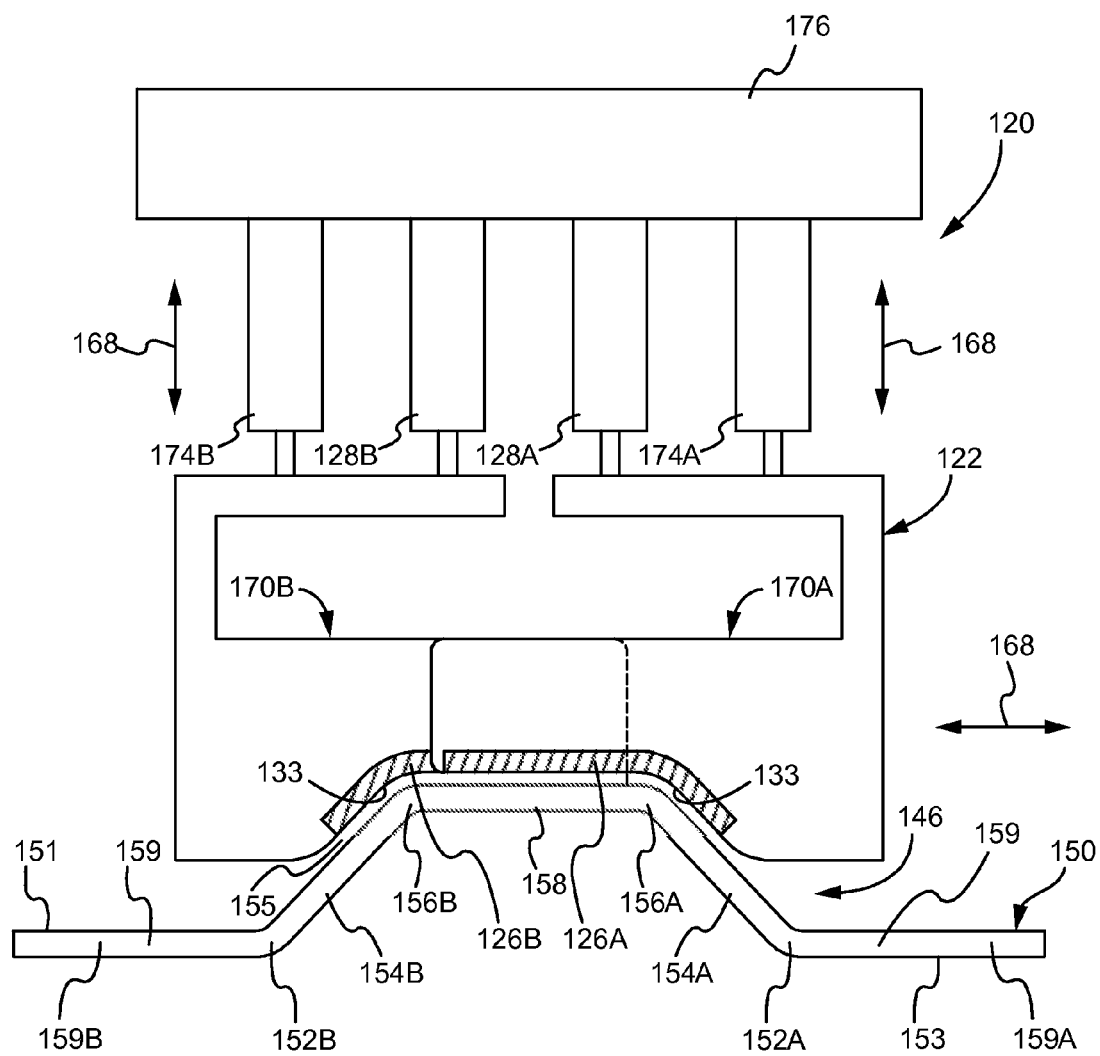
FIG. 3 is a schematic side view of an apparatus for inspecting a component according to one embodiment showing a first feature inspector.
Figure 4:
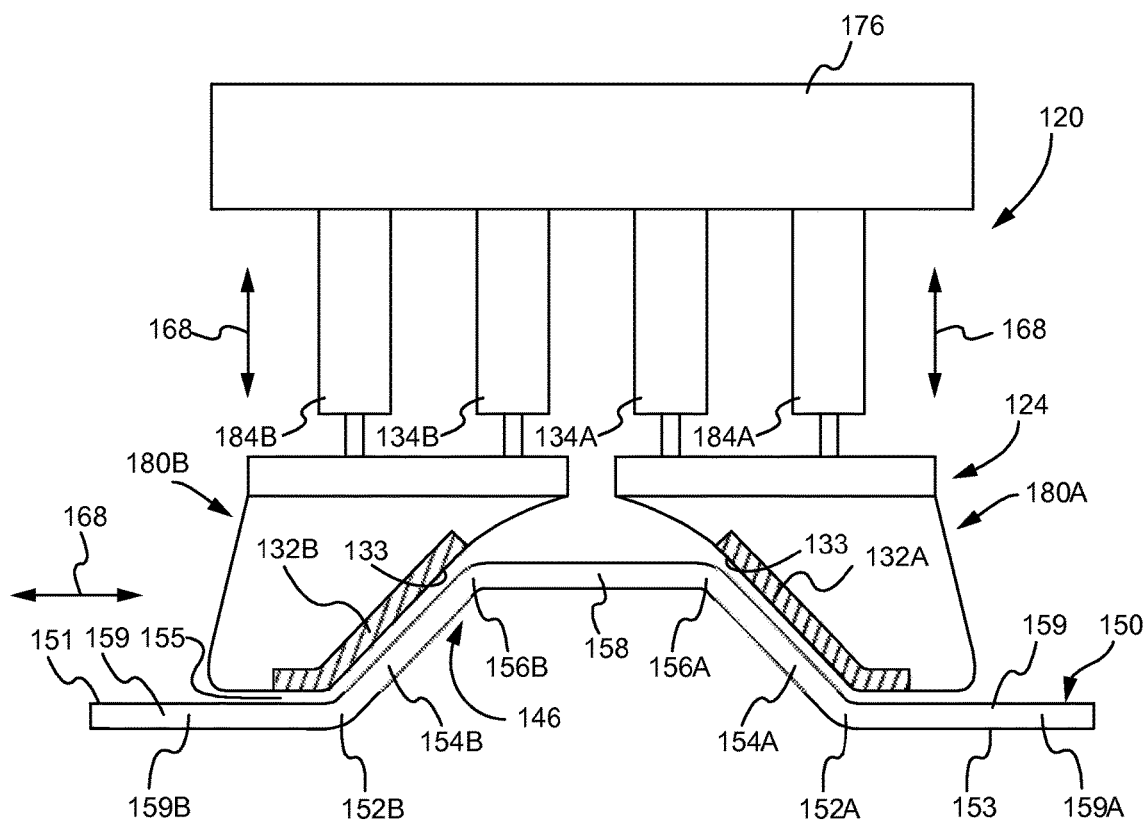
FIG. 4 is a schematic side view of an apparatus for inspecting a component according to one embodiment showing a second feature inspector.

Referring to FIG. 1, according to one embodiment, a system 100 for inspecting a component 150 is shown. The system 100 includes a probe 120 coupled to an actuator 140, which is controlled by a controller 130. The actuator 140 is controlled by the controller 130 to position the probe 120 in a desired inspection position relative to a 3-dimensional structure 146 of the component 150 in order to non-destructively inspect the 3-dimensional structure. As shown in FIGS. 3 and 4, in one implementation, the desired inspection position can be a position in which emission/detection surfaces 133 of the wave transducers 126A, 126B, 132A, 132B of the probe 120 are parallel to an outer surface 151 of the respective feature of the 3-dimensional structure 146 to be tested, and spaced-apart from the outer surface of the respective feature of the 3-dimensional structure to be tested to create a gap 155 of a desired thickness between the emission/detection surfaces of the wave transducers and the outer surface that remains constant along the entire length of the wave transducers. With the probe 120 in the desired inspection position, the actuator 140 moves the probe 120 along the 3-dimensional structure 146 in a testing direction 160.

As the probe 120 moves along the 3-dimensional structure 146, each wave transducer 126A, 126B, 132A, 132B of the probe emits acoustic waves into the 3-dimensional structure and receives acoustic waves from the 3-dimensional structure. Although not shown, a couplant, such as water, oil, propylene glycol, glycerin, gel, and the like, is positioned within the gap 155 between the wave transducers 126A, 126B, 132A, 132B and the outer surface 151 of the component 150. The couplant provides a medium that facilitates the transmission of the acoustic waves (e.g., sound energy) between the wave transducers 126A, 126B, 132A, 132B and the outer surface 151.

The wave transducers 126A, 126B, 132A, 132B can be any of various wave transducers for emitting and receiving acoustic waves. According to some embodiments, the wave transducers emit and receive ultrasonic waves. Generally, the acoustic waves generated and emitted by the wave transducers 126A, 126B, 132A, 132B are transmitted into the 3-dimensional structure 146. After passing through the couplant, the acoustic waves propagate through the 3-dimensional structure 146 from the outer surface 151 (e.g., front surface) to an opposing back surface 153. Then, the acoustic waves reflect off of the back surface 153, and propagate back to the outer surface 151. From the outer surface 151, the reflected waves pass through the couplant and are received by the wave transducers 126A, 126B, 132A, 132B. The pulse characteristics (e.g., amplitude) of the acoustic waves generated by the wave transducers 126A, 126B, 132A, 132B are compared to the pulse characteristics of the acoustic waves received by the wave transducers (e.g. after passing through the 3-dimensional structure 146) to determine if defects exist in the structure.

Because the pulse characteristics of the acoustic waves can change with changes in the thickness of the gap 155 between the wave transducers 126A, 126B, 132A, 132B and the outer surface 151 (e.g., because the distance acoustic waves must travel changes), the thickness of the gap along the length of the wave transducers is desirably held constant as the probe 120 is moved along the 3-dimensional structure 146. Non-uniformity in the thickness of the gap 155 between the wave transducers 126A, 126B, 132A, 132B and the outer surface 151 along the length of the wave transducers, such as due to angling of the emission/detection surfaces 133 of the transducers relative to the outer surface 151 caused by tilting (e.g., pitching and rolling) of the component relative to the probe, may result in inspection errors. In some cases, sufficient non-uniformity in the thickness of the gap 155 may result in an attenuation of the acoustic waves between the emission/detection surfaces 133 of the wave transducers and the outer surface 151, or failure of the acoustic waves to transmit between the emission/detection surfaces and the outer surface.

Figure 6:
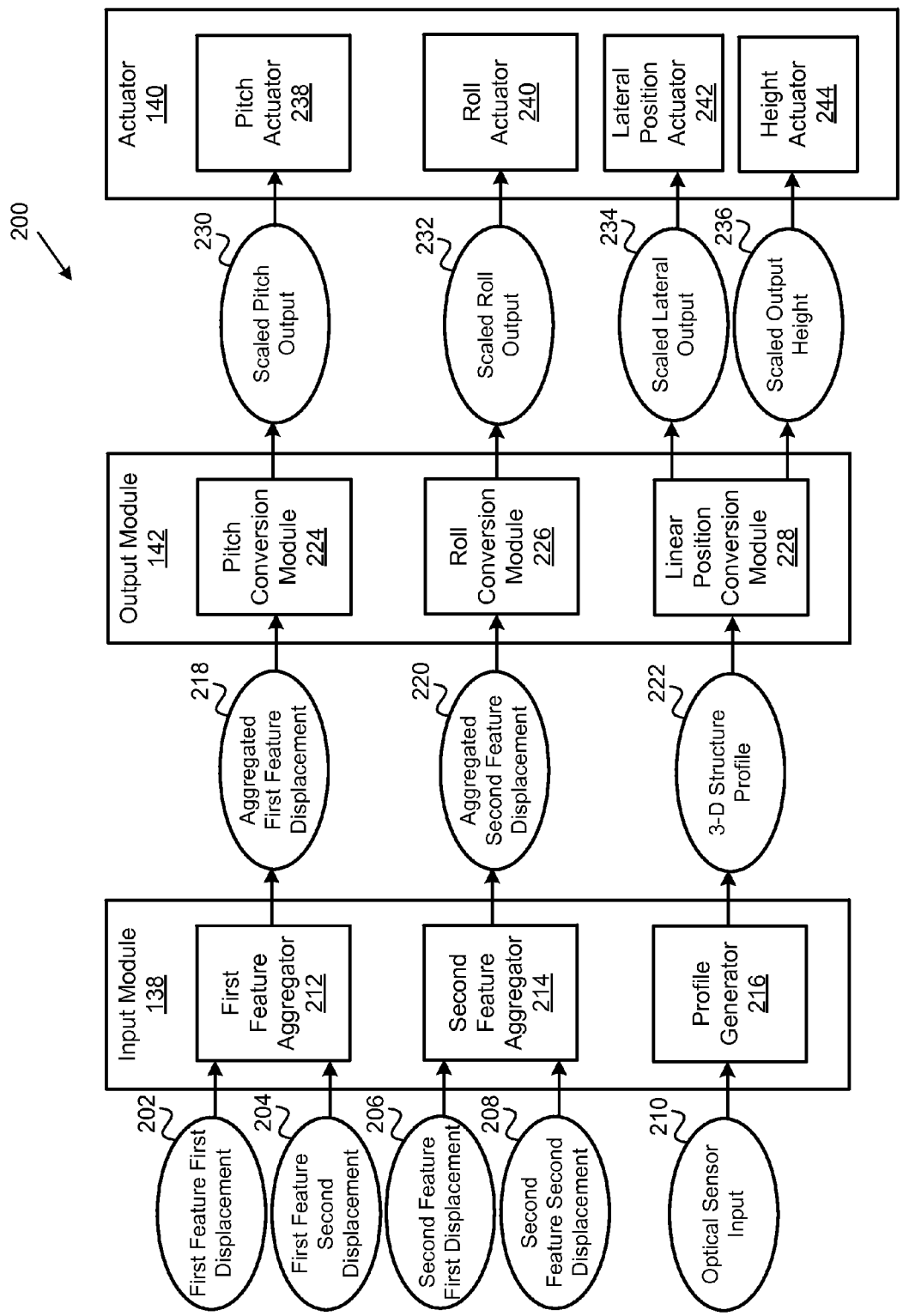
FIG. 6 is a schematic flow diagram of a system for inspecting a component according to one embodiment.

The actuator 140, which may be a robotic arm 144 in some implementations, is actuatable to adjust the position of the probe 120 to maintain the gap 155 at the desired thickness as the probe 120 moves in the testing direction along the 3-dimensional structure 146. The type of adjustment to the position of the probe 120 depends on the size, shape, and orientation of the 3-dimensional structure 146. In some implementations, the actuator 140 is configured to adjust one or more of a lateral position of the probe 120 as indicated by directional arrows 162, a pitch of the probe as indicated by directional arrows 166, a roll of the probe as indicated by directional arrows 164, and a height of the probe as indicated by directional arrows 168. Referring to FIG. 6, the actuator 140 can include a pitch actuator 238, roll actuator 240, lateral position actuator 242, and height actuator 244. The pitch actuator 238 is actuated to adjust the pitch of the probe 120, the roll actuator 240 is actuated to adjust the roll of the probe, the lateral position actuator 242 is actuated to adjust the lateral position of the probe, and the height actuator 244 is actuated to adjust the height of the probe, all relative to the 3-dimensional structure. The pitch actuator 238, roll actuator 240, lateral position actuator 242, and height actuator 244 can be any of various actuators known in the art. According to one implementation, the pitch actuator 238, roll actuator 240, lateral position actuator 242, and height actuator 244 form part of a robotic arm manufactured by Kuka®.

Adjustment of the position of the probe 120 using the actuator 140 is based at least partially, and in some cases solely, on input from displacement sensors 128A, 128B, 134A, 134B forming part of the probe. In this manner, a predetermined or preloaded model of the component, including predetermined teach paths, is not needed or relied upon to inspect the component. The displacement sensors 128A, 128B, 134A, 134B detect displacement of the wave transducers 126A, 126B, 132A, 132B, respectively, with respect to the outer surface 151 of the 3-dimensional structure 146 of the component 150. The displacement sensors 128A, 128B, 134A, 134B can be any of various types of displacement sensors. In some implementations, each displacement sensor 128A, 128B, 134A, 134B is a linear variable differential transformer (LVDT) sensor. Generally, a displacement sensor, such as an LVDT sensor, converts a linear displacement, relative to a reference point, into a proportional electrical signal. The electrical signal includes phase and amplitude information. The phase information indicates the direction of displacement and the amplitude information indicates the distance of displacement.

The probe 120 includes one or both of first and second feature inspectors 122, 124, and may include more than two feature inspectors depending on the configuration of the 3-dimensional structure 146. The first feature inspector 122 includes the wave transducers 126A, 126B, and the displacement sensors 128A, 128B. Similarly, the second feature inspector 124 includes the wave transducers 132A, 132B and the displacement sensors 134A, 134B. The displacement sensors 128A, 128B of the first feature inspector 122 are movably and separately coupled to the wave transducers 126A, 126B, respectively. The displacement sensors 134A, 134B of the second feature inspector 124 are movably and separately coupled to the wave transducers 132A, 132B, respectively. The first feature inspector 122 is configured to inspect a first feature of the 3-dimensional structure 146 of the component 150. Accordingly, the wave transducers 126A, 126B of the first feature inspector 122 are configured to emit acoustic waves into and receive acoustic waves from the first feature of the 3-dimensional structure 146. The second feature inspector 124 is configured to inspect a second feature of the 3-dimensional structure 146 of the component 150. Accordingly, the wave transducers 132A, 132B of the second feature inspector 124 are configured to emit acoustic waves into and receive acoustic waves from the second feature of the 3-dimensional structure 146.

In addition to, or alternatively of, the displacement sensors 128A, 128B, 134A, 134B, adjustment of the position of the probe 120 using the actuator 140 can be based at least partially on input from at least one optical sensor 136. In some implementations, the probe 120 includes an optical sensor 136 configured to detect a profile of the 3-dimensional structure 146. The profile of the 3-dimensional structure 146 may include a size and shape of the outer surface 151 of the 3-dimensional structure 146. The optical sensor 136 can be configured to detect the profile of the 3-dimensional structure 146, including one or more of the first feature and second feature, or additional features of the 3-dimensional structure. Although a single optical sensor 136 is shown, in some embodiments, the probe 120 may include multiple optical sensors 136, such as two optical sensors spaced apart in the testing direction 160. According to one implementation, the optical sensor 136 is a laser sensor, such as manufactured by Keyence®.

The component 150 can be any of various components made from any of various materials. In some implementations, the component 150 is made from a metal, such as steel and aluminum. In other implementations, the component 150 is made from a non-metal, such as graphite, composite, ceramic, polymeric, and the like. The 3-dimensional structure 146 likewise can be any of various 3-dimensional structures. As defined herein, a 3-dimensional structure is a non-flat or substantially non-flat structure. Defined another way, a 3-dimensional structure is a protrusion that protrudes relative to a flat or substantially non-flat plane of reference.

Figure 2:
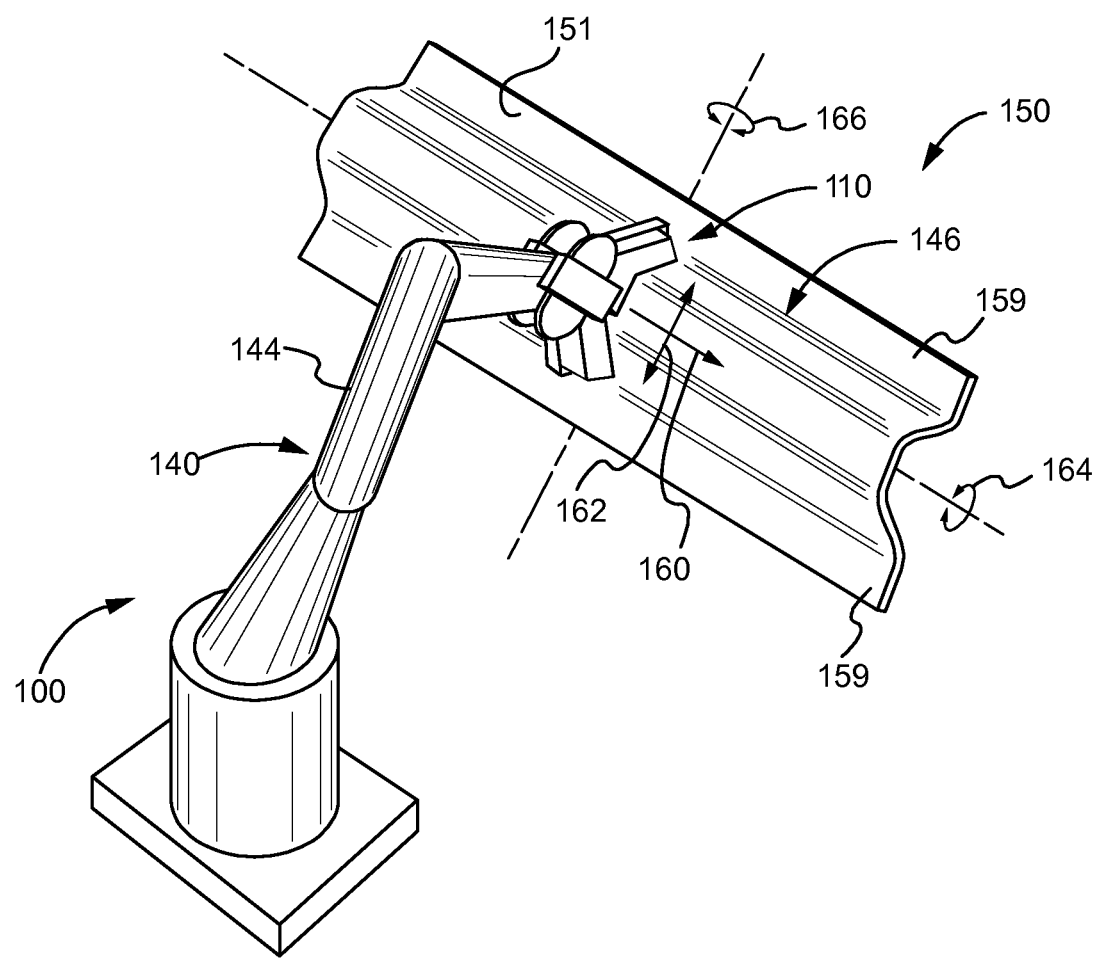
FIG. 2 is a perspective view of a system for inspecting a component according to one embodiment.

As shown in FIGS. 2 and 3, the component 150 can be an aircraft stringer and the 3-dimensional structure 146 can be a raised or hat portion of the stringer. In other embodiments, the component 150 can be any of various components or parts, such as stiffeners, of any of various objects, such as vehicles, and the 3-dimensional structure 146 can be of various structures with any of various sizes and shapes. In the illustrated embodiment, the 3-dimensional structure 146 is positioned between two flanges 159, which are substantially flat relative to the 3-dimensional structure. In other words, the 3-dimensional structure 146 protrudes or is raised relative to the flanges 159. The 3-dimensional structure 146 includes a first feature and a second feature. The first feature of the 3-dimensional structure 146 is a cap 158, and the second feature of the 3-dimensional structure are opposing webs 154A, 154B. The webs 154A, 154B couple the cap 158 to the flanges 159. As shown, the webs 154A, 154B are angled with respect to the cap 158 and flanges 159. The webs 154A, 154B are angled between 0-degree and 90-degrees with respect to the cap 158 and flanges 159 in some embodiments. The 3-dimensional structure 146 also includes lower radii 152A, 152B defining a transition between the flanges 159 and respective webs 154A, 154B, and upper radii 156A, 156B defining a transition between the webs and the cap 158. The component 150 is elongate in the testing direction 160 such that a width of the component in the lateral direction 162 is much smaller than a length of the component in the testing direction.

Referring to FIG. 3, according to one embodiment, the first feature inspector 122 includes first and second housings 170A, 170B. The first and second housings 170A, 170B are spaced longitudinally (e.g., in the testing direction 160) apart from each other along the cap 158. Each first and second housing 170A, 170B houses a respective one of the wave transducers 126A, 126B. Moreover, each wave transducer 126A, 126B can include an array of wave transducers, such that the first housing 170A includes an array of wave transducers 126A and the second housing 170B includes an array of wave transducers 126B.

The wave transducers 126A, 126B are configured to be normal to and at a constant distance away from the outer surface 151 of the portion of the component 150 being inspected when the probe 120 is in the desired inspection position. In the present embodiment, each of the wave transducers 126A, 126B is configured to inspect at least a portion of the cap 158 and a respective one of the upper radii 156A, 156B of the 3-dimensional structure 146. Accordingly, the wave transducers 126A, 126B are shaped to compliment (e.g., match) the shape of the cap 158 and respective upper radii 156A, 156B. Moreover, the first and second housings 170A, 170B, along with the corresponding wave transducers 126A, 126B, are positioned on opposing sides of the 3-dimensional structure 146. For example, from the vantage point of FIG. 3, the first housing 170A and wave transducer 126A are positioned on the right side of the 3-dimensional structure 146, and downstream of the second housing 170B and wave transducer 126B relative to the testing direction 160. In contrast, the second housing 170B and wave transducer 126B are positioned on the left side of the 3-dimensional structure 146, and upstream of the first housing 170A and wave transducer 126A relative to the testing direction 160. Also, each of the wave transducers 126A, 126B can extend across more than half of a width of the cap 158 such that portions of the wave transducers 126A, 126B may longitudinally overlap.

The probe 120 includes a base 176 that is coupled to a portion of the actuator 140. In one embodiment, the actuator 140 is a robotic arm 144, and the base 176 is coupled to an end effector of the robotic arm 144. The actuator 140 is actuatable to move the base 176 relative to the component 150. The first and second housings 170A, 170B are coupled to the base 176 via respective biasing elements 174A, 174B. Each of the biasing elements 174A, 174B applies a force to the respective first and second housings 170A, 170B to bias the first and second housings away from the base 176 toward the outer surface 151 of the component 150. The base 176 of the probe 120 is positioned such that the first and second housings 170A, 170B, including the wave transducers 126A, 126B, are biased against the outer surface 151 of the cap 158 and respective upper radii 156A, 156B. In this manner, with a couplant positioned between the wave transducers 126A, 126B and the outer surface 151 of the cap 158 and respective upper radii 156A, 156B, the wave transducers 126A, 126B are maintained in indirect contact with the outer surface of the cap and respective upper radii. The biasing elements 174A, 174B can be passive biasing elements, such as springs, or active biasing elements, such as pneumatically or hydraulically controlled shock absorbers.

With a vertical position of the base 176 remaining relatively constant, and the wave transducers 126A, 126B biased into contact with the outer surface 151 of the cap 158 and respective upper radii 156A, 156B, any pitching of the component 150 would cause the first and second housings 170A, 170B to move vertically, as indicated by directional arrows 168, toward or away from the base 176. More specifically, if the component 150 is pitching away from the base 176 in the testing direction 160, then the bias against the first and second housings 170A, 170B will cause the first and second housings to move away from the base. In contrast, if the component 150 is pitching toward the base 176 in the testing direction 160, then the outer surface 151 of the cap 158 applies an opposing force to the first and second housings 170A, 170B greater than the biasing force of the biasing elements 174A, 174B, which causes the first and second housings to move toward the base 176.

Movement of the first and second housings 170A, 170B relative to the base results in displacement of the first and second displacement sensors 128A, 128B, respectively. Displacement of the first and second displacement sensors 128A, 128B correspondingly results in respective output signals (e.g., voltages) proportional to and in phase with the displacement. The output signals from the first and second displacement sensors 128A, 128B are electrically communicated to an input module 138 of the controller 130.

Referring to FIG. 4, according to one embodiment, the second feature inspector 124 includes first and second housings 180A, 180B. The first and second housings 180A, 180B are spaced laterally (e.g., in the direction 162) apart from each other across the cap 158. Each first and second housing 180A, 180B houses a respective one of the wave transducers 132A, 132B. Moreover, each wave transducer 132A, 132B can include an array of wave transducers, such that the first housing 180A includes an array of wave transducers 132A and the second housing 180B includes an array of wave transducers 132B.

The wave transducers 132A, 132B are configured to be normal to and at a constant distance away from the outer surface 151 of the portion of the component 150 being inspected when the probe 120 is in the desired inspection position. In the present embodiment, each of the wave transducers 132A, 132B is configured to inspect a respective one of the webs 154A, 154B and a respective one of the lower radii 152A, 152B of the 3-dimensional structure 146. Accordingly, each of the wave transducers 132A, 132B is shaped to compliment (e.g., match) the shape of a respective web 154A, 154B and respective lower radii 152A, 152B. Moreover, the first and second housings 180A, 180B, along with the corresponding wave transducers 132A, 132B, are positioned on opposing sides of the 3-dimensional structure 146. For example, from the vantage point of FIG. 4, the first housing 180A and wave transducer 132A are positioned on the right side of the 3-dimensional structure 146 and the second housing 180B and wave transducer 132B are positioned on the left side of the 3-dimensional structure.

The first and second housings 180A, 180B of the second feature inspector 124 are coupled to the base 176 via respective biasing elements 184A, 184B configured similarly to the biasing elements 174A, 174B. For example, each of the biasing elements 184A, 184B applies a force to the respective first and second housings 180A, 180B to bias the first and second housings away from the base 176 toward the outer surface 151 of the respective webs 154A, 154B and lower radii 152A, 152B. The base 176 of the probe 120 is positioned such that the first and second housings 180A, 180B, including the wave transducers 132A, 132B, are biased against the outer surface 151 of the respective webs 154A, 154B and lower radii 152A, 152B. In this manner, with a couplant positioned between the wave transducers 132A, 132B and the outer surface 151 of the respective webs 154A, 154B and lower radii 152A, 152B, the wave transducers are maintained in indirect contact with the outer surface 151 of the respective webs and lower radii. Like the biasing elements 174A, 174B, the biasing elements 184A, 184B can be passive biasing elements, such as springs, or active biasing elements, such as pneumatically or hydraulically controlled shock absorbers.

With a vertical position of the base 176 remaining relatively constant, and the wave transducers 132A, 132B biased into contact with the outer surface 151 of the of the respective webs 154A, 154B and lower radii 152A, 152B, any rolling of the component 150 would cause one of the first and second housings 180A, 180B to move vertically toward the base and the other of the first and second housings to move vertically away from the base, as indicated by directional arrows 168. More specifically, if the component 150 is rolling in a clockwise direction relative to the base 176, then the bias against the first housing 180A will cause the first housing to move away from the base, and will cause the outer surface 151 of the web 154B to apply an opposing force to the second housing 180B greater than the biasing force of the biasing element 184B, which causes the second housing to move toward the base 176. In contrast, if the component 150 is rolling in a counterclockwise direction relative to the base 176, then the bias against the second housing 180B will cause the second housing to move away from the base, and will cause the outer surface 151 of the web 154A to apply an opposing force to the first housing 180A greater than the biasing force of the biasing element 184A, which causes the first housing to move toward the base 176.

Movement of the first and second housings 180A, 180B relative to the base results in opposing displacement of the first and second displacement sensors 134A, 134B, respectively. Opposing displacement of the first and second displacement sensors 134A, 134B correspondingly results in respective output signals (e.g., voltages) proportional to and in phase with the displacements. The output signals from the first and second displacement sensors 134A, 134B are electrically communicated to the input module 138 of the controller 130.

Figure 5:
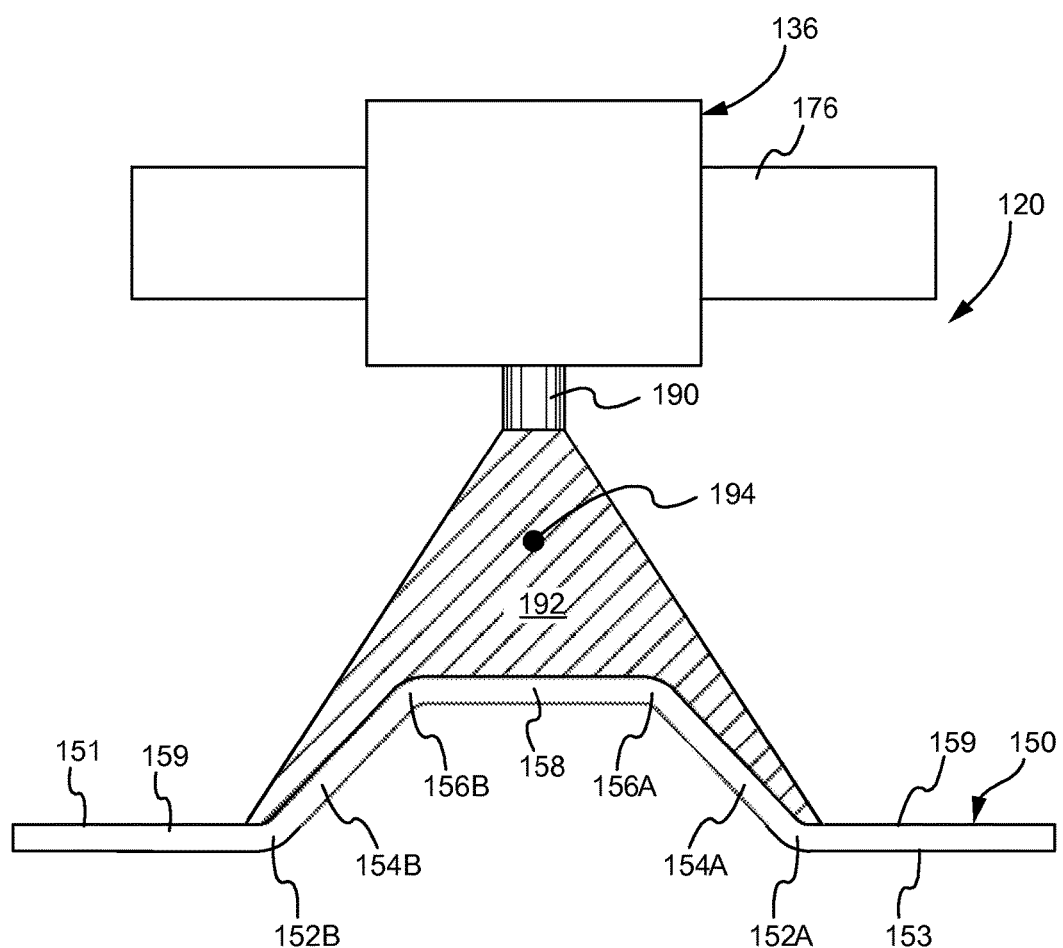
FIG. 5 is a schematic side view of an apparatus for inspecting a component according to one embodiment showing an optical sensor.

Referring to FIG. 5, one or more optical sensors 136 can be coupled to the base 176. In some implementations, the optical sensor 136 is fixed to the base 176. The optical sensor 136 generates an optical beam 192 that can be generated by an optical beam source 190. In one implementation, the optical beam 192 is a laser beam. The optical beam 192 reflects off of the outer surface 151 of the 3-dimensional structure 146, and the reflected beam is received by the optical sensor 136. Based on the characteristics of the reflected beam, a profile of the 3-dimensional structure 146 is determined. Then, a reference point 194 positionally tied to specific features of the determined profile of the 3-dimensional structure 146 can be determined. For example, according to one embodiment, the reference point 194 is the intersection between two virtual planes that are co-planar with the webs 154A, 154B. As the profile of the 3-dimensional structure 146 changes, the position of the reference point 194 will correspondingly change. Therefore, in one embodiment, the optical sensor 136 is configured to detect changes in the profile of the 3-dimensional structure 146 by monitoring changes in the position of the reference point 194. The changes in the profile of the 3-dimensional structure 146 detected by the optical sensor 136 are converted to output signals that are communicated to the input module 138 of the controller 130. The controller 130 then controls the actuator 140 to ensure proper alignment of the probe 120 with the 3-dimensional structure 146, and to ensure a desirable gap 155 between the transducers and the outer surface 151 of the 3-dimensional structure as will be described in more detail below.

In some embodiments, the probe 120 includes at least two optical sensors 136 spaced longitudinally apart along the length of the component 150. Each optical sensor 136 continuously determines a profile of the 3-dimensional structure 146 at longitudinally spaced-apart points along the length of the component. More specifically, each optical sensor 136 continuously detects real-time profiles of the 3-dimensional structure 146 and provides dynamic feedback as the probe 120 moves along the 3-dimensional structure. The profiles determined by the optical sensors 136 can be compared to aid in determining a pitch and/or roll of the component 150. For example, when a detected profile of the 3-dimensional structure 146 at a first location along the structure is positioned vertically higher or lower than a detected profile of the 3-dimensional at a second location along the structure, a pitch of the component may be indicated. In a similar manner, when a detected profile of the 3-dimensional structure 146 at a first location along the structure is angled and a detected profile of the 3-dimensional structure 146 at a second location along the structure is angled similarly, a roll of the component may be indicated.

Although the illustrated embodiments show a system 100 having a single probe 120 with one base 176 to which the first and second housings 170A, 170B, first and second housings 180A, 180B, and optical sensors 136 are coupled, in some embodiments, the system 100 includes multiple probes each with a base 176 to which the first and second housings 170A, 170B, first and second housings 180A, 180B, and optical sensors 136, respectively, are coupled. Additionally, although the 3-dimensional structure 146 shown is a symmetrical cap 158 with symmetrical webs 154A, 154B, and the probe 120 includes two feature inspectors, each with two wave transducers, for inspecting the symmetrical cap and symmetrical webs, respectively, in some embodiments, the 3-dimensional structure may have more or less than two features, which may be symmetrical or non-symmetrical, and the probe may have more or less than two feature inspectors, each with more or less than two wave transducers, for inspecting the 3-dimensional structure with more or less than two features.

An output module 142 of the controller 130 converts the output signals from the displacement sensors 128A, 128B, 134A, 134B and optical sensor 136 received by the input module 138 into command signals for actuating the actuator 140. More specifically, in one implementation, the output module 142 converts the signals from the displacement sensors 128A, 128B into a pitch command for adjusting the pitch of the probe 120 via actuation of the actuator 140, and the output module 142 converts the signals from the displacement sensors 134A, 134B into a roll command for adjusting the roll of the probe 120 via actuation of the actuator 140. In some implementations, the output module 142 converts the signals from the optical sensor 136 into a lateral and/or height command for adjusting the lateral position or height of the probe 120 via actuation of the actuator 140. In yet one implementation, the output module 142 converts the signals from the optical sensor 136 into a pitch and/or roll command for adjusting the pitch and/or roll of the probe 120 via actuation of the actuator 140.

Referring to FIG. 6, another embodiment of a system 200 for inspecting a component is shown. The system 200 includes the input module 138, which includes a first feature aggregator 212, a second feature aggregator 214, and a profile generator 216. The first feature aggregator 212 receives a first feature first displacement 202 and a first feature second displacement 204. The first feature first displacement 202 corresponds with a detected displacement of a first wave transducer relative to a first feature of a structure being inspected. The first feature second displacement 204 corresponds with a detected displacement of a second wave transducer relative to the first feature of the structure being inspected. The first wave transducer and the second wave transducer can be independently displaceable. Additionally, the first feature can include a surface that is substantially perpendicular to the vertical direction indicated by direction arrows 168.

The second feature aggregator 214 receives a second feature first displacement 206 and a second feature second displacement 208. The second feature first displacement 206 corresponds with a detected displacement of a third wave transducer relative to a second feature of a structure being inspected. The second feature second displacement 208 corresponds with a detected displacement of a fourth wave transducer relative to the second feature of the structure being inspected. The third wave transducer and the fourth wave transducer can be independently displaceable. Additionally, the second feature can include a surface that is substantially vertically angled with respect to the lateral direction 162 indicated by directional arrows.

The displacements 202, 204, 206, 208 can be output signals from respective displacement sensors each coupled to a respective one of the first, second, third, and fourth wave transducers. Each output signal can be a voltage that is proportional to the displacement detected by the associated displacement sensor.

The first feature aggregator 212 aggregates the first feature first displacement 202 and the first feature second displacement 204 to determine an aggregated first feature displacement 218. Aggregation of the first feature first displacement 202 and the first feature second displacement 204 can include combining or correlating the displacements via any of various operations as desired, such as summing, averaging, subtracting, and the like. In one implementation, the first feature aggregator 212 includes a differential amplifier that determines the aggregated first feature displacement 218 by calculating a difference between the first feature first displacement 202 and the first feature second displacement 204. The aggregated first feature displacement 218 can be equal to the difference between the first feature first displacement 202 and the first feature second displacement 204.

The second feature aggregator 214 aggregates the second feature first displacement 206 and the second feature second displacement 208 to determine an aggregated second feature displacement 220. Aggregation of the second feature first displacement 206 and the second feature second displacement 208 can include combining or correlating the displacements via any of various operations as desired, such as summing, averaging, subtracting, and the like. In one implementation, the second feature aggregator 214 includes a differential amplifier that determines the aggregated second feature displacement 220 by calculating a difference between the second feature first displacement 206 and the second feature second displacement 208. The aggregated second feature displacement 220 can be equal to the difference between the second feature first displacement 206 and the second feature second displacement 208.

The profile generator 216 determines a 3-dimensional structure profile 222 of the 3-dimensional structure 146 based on the optical sensor input 210. The 3-dimensional structure profile 222 can include information regarding the entire profile of the 3-dimensional structure 146 and/or the location of a reference point positionally tied to the determined profile of the structure.

In some implementations, one or more of the aggregated first feature displacement 218, aggregated second feature displacement 220, and 3-dimensional structure profile 222 are fed directly to the actuator 140 as input to control the angular position (e.g., pitch and roll) and linear position (e.g., lateral position or height), respectively, of an end effector of the actuator. However, in other implementations, the aggregated first feature displacement 218, aggregated second feature displacement 220, and 3-dimensional structure profile 222 are scaled before being sent as input to the actuator 140. For example, the output module 142 may include a pitch conversion module 224, roll conversion module 226, and linear position conversion module 228. The pitch conversion module 224 converts the aggregated first feature displacement 218 into a scaled pitch output 230. The roll conversion module 226 converts the aggregated second feature displacement 220 into a scaled roll output 232. The linear position conversion module 228 converts the 3-dimensional structure profile 222 into a scaled lateral output 234 and scaled height output 236.

Conversion of the aggregated first feature displacement 218, aggregated second feature displacement 220, and 3-dimensional structure profile 222 into the scaled pitch output 230, scaled roll output 232, scaled lateral output 234, and scaled height output 236, respectively, includes scaling the aggregated first feature displacement 218, aggregated second feature displacement 220, and 3-dimensional structure profile 222 to ensure actual movement of the actuator 140, and probe 120, is correlated to the aggregated displacements and 3-dimensional structure profile. For example, in one implementation, the aggregated first feature displacement 218 and aggregated second feature displacement 220 is scaled such that one degree of displacement detected by the displacement sensors correlates to one degree of opposite compositional movement of the actuator 140 and probe 120. The need for and magnitude of scaling depends on the characteristics of the input voltages for controlling the actuator 140 in view of the output voltages of the displacement sensors. The pitch actuator 238, roll actuator 240, lateral position actuator 242, and height actuator 244 of the actuator 140 receive the scaled pitch output 230, scaled roll output 232, scaled lateral output 234, and scaled height output 236, respectively, and actuate accordingly.

Figure 7:
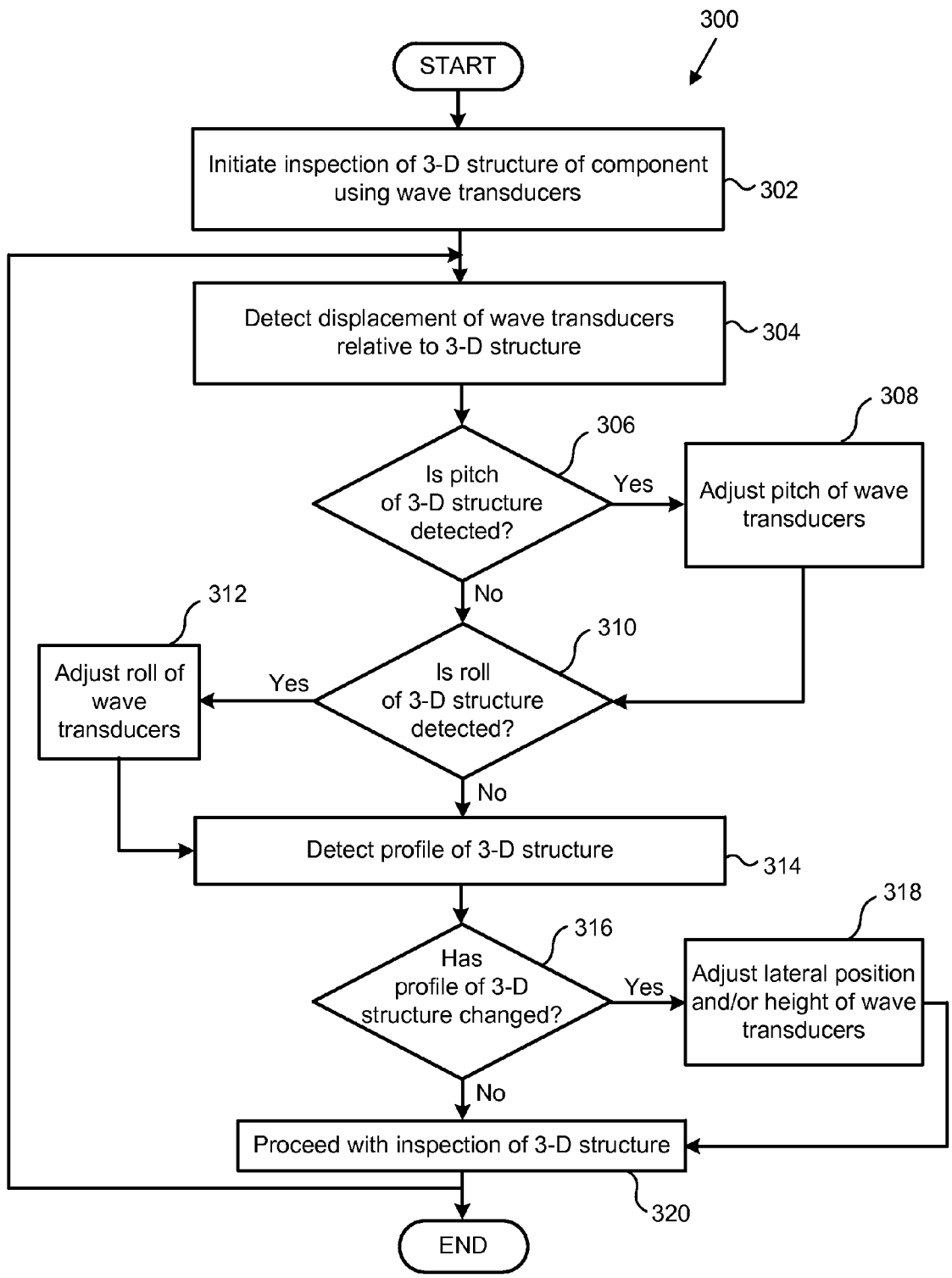
FIG. 7 is a schematic flow diagram of a method for inspecting a component according to one embodiment.

Referring to FIG. 7, according to one embodiment, a method 300 for inspecting a component includes initiating an inspection of a 3-dimensional structure of the component using at least one wave transducer at 302. In one implantation, initiating the inspection of the 3-dimensional structure at 302 includes positioning a probe at a start point relative to the 3-dimensional structure. Positioning the probe at the start point may include using a CAD model of the 3-dimensional structure to determine a desired start point and moving the probe to the desired start point. The method 300 also includes detecting displacement of the at least one wave transducer relative to the 3-dimensional structure at 304. Additionally, the method 300 includes determining if pitching of the 3-dimensional structure is detected at 306. If pitching of the 3-dimensional structure is detected at 306, the method 300 adjusts the pitch of the wave transducers at 308 to compensate for the pitching of the 3-dimensional structure. The method 300 also includes determining if rolling of the 3-dimensional structure is detected at 310. If rolling of the 3-dimensional structure is detected at 310, the method 300 adjusts the roll of the wave transducers at 312 to compensate for the rolling of the 3-dimensional structure. Determining if pitching or rolling of the 3-dimensional structure at 306, 310 can be based on displacement of the wave transducers relative to the 3-dimensional structure being detected at 304. Detection of displacement of the wave transducers can be accomplished by displacement sensors coupled to the respective wave transducers. Adjustment of the pitch and roll of the wave transducers can be accomplished by adjusting the pitch and roll of an end effector of an actuator to which the wave transducers are coupled.

The method 300 may also include detecting a profile, or reference point tied to the profile, of the 3-dimensional structure at 314. Based on the profile, or reference point tied to the profile, of the 3-dimensional structure, the method 300 determines if the profile or reference point has changed at 316. If the profile or reference point has changed at 316, then the method 300 adjusts a linear position (e.g., lateral position or height) of the wave transducers at 318 to compensate for a change in the linear position of the 3-dimensional structure. Adjustment of the linear position of the wave transducers can be accomplished by adjusting the linear position of an end effector of an actuator to which the wave transducers are coupled.

Should any of the steps 306, 310, 316 be determined in the affirmative and following associated adjustment at 308, 312, 318, respectively, alignment and a uniform gap with a desired thickness between a probe and the 3-dimensional structure is ensured and the method 300 proceeds with the inspection of the 3-dimensional structure at 320. If the inspection of the 3-dimensional structure is not completed, the method 300 then returns to step 304. Similarly, if none of the steps 306, 310, 316 is determined in the affirmative, alignment and a uniform gap with a desired thickness between the probe and the 3-dimensional structure is assumed and the method 300 proceeds with the inspection of the 3-dimensional structure at 320. Again, if the inspection of the 3-dimensional structure is not completed, the method 300 then returns to step 304. However, if inspection of the 3-dimensional structure is completed following step 320, then the method 300 ends.

Figure 8:
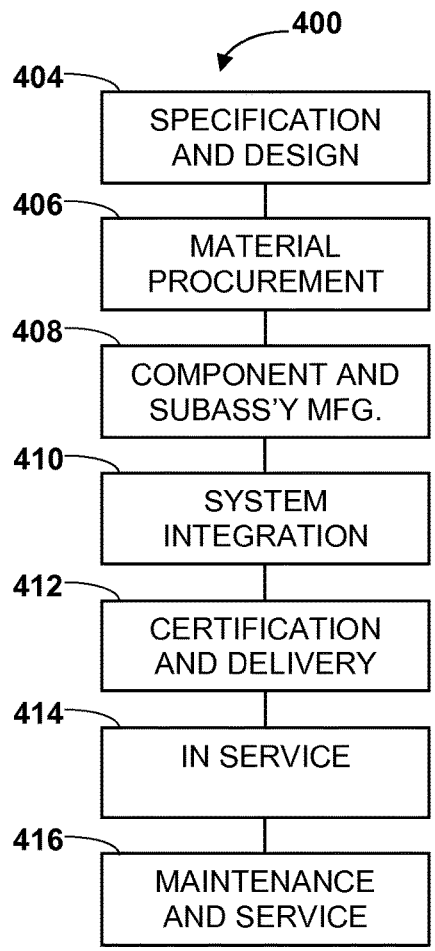
FIG. 8 is a flow diagram of aircraft production and service methodology.
Figure 9:
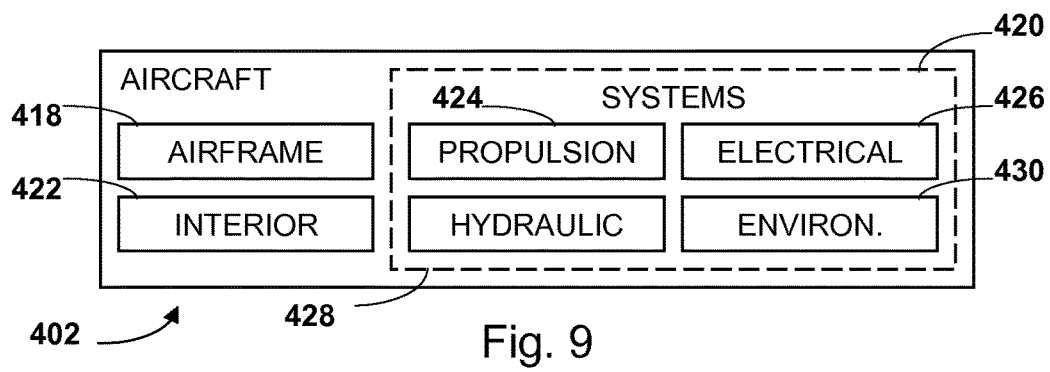
FIG. 9 is a block diagram of an aircraft.

Referring more particularly to the drawings, embodiments of the disclosure may be described in the context of an aircraft manufacturing and service method 400 as shown in FIG. 8 and an aircraft 402 as shown in FIG. 9. During pre-production, exemplary method 400 may include specification and design 404 of the aircraft 402 and material procurement 406. During production, component and subassembly manufacturing 408 and system integration 410 of the aircraft 402 takes place. Thereafter, the aircraft 402 may go through certification and delivery 412 in order to be placed in service 414. While in service by a customer, the aircraft 402 is scheduled for routine maintenance and service 416 (which may also include modification, reconfiguration, refurbishment, and so on).

Each of the processes of method 400 may be performed or carried out by a system integrator, a third party, and/or an operator (e.g., a customer). For the purposes of this description, a system integrator may include without limitation any number of aircraft manufacturers and major-system subcontractors; a third party may include without limitation any number of venders, subcontractors, and suppliers; and an operator may be an airline, leasing company, military entity, service organization, and so on.

As shown in FIG. 9, the aircraft 402 produced by exemplary method 400 may include an airframe 418 with a plurality of systems 420 and an interior 422. Examples of high-level systems 420 include one or more of a propulsion system 424, an electrical system 426, a hydraulic system 426, and an environmental system 430. Any number of other systems may be included. Although an aerospace example is shown, the principles of the invention may be applied to other industries, such as the automotive industry.

Apparatus and methods embodied herein may be employed during any one or more of the stages of the production and service method 400. For example, components or subassemblies corresponding to production process 408 may be fabricated or manufactured in a manner similar to components or subassemblies produced while the aircraft 402 is in service. Also, one or more apparatus embodiments, method embodiments, or a combination thereof may be utilized during the production stages 408 and 410, for example, by substantially expediting assembly of or reducing the cost of an aircraft 402. Similarly, one or more of apparatus embodiments, method embodiments, or a combination thereof may be utilized while the aircraft 402 is in service, for example and without limitation, to maintenance and service 416.

Unless otherwise indicated, the terms "first," "second," etc. are used herein merely as labels, and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

In the above description, certain terms may be used such as "up," "down," "upper," "lower," "horizontal," "vertical," "left," "right," "over," "under" and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object. Further, the terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise. Further, the term "plurality" can be defined as "at least two."

Additionally, instances in this specification where one element is "coupled" to another element can include direct and indirect coupling. Direct coupling can be defined as one element coupled to and in some contact with another element. Indirect coupling can be defined as coupling between two elements not in direct contact with each other, but having one or more additional elements between the coupled elements. Further, as used herein, securing one element to another element can include direct securing and indirect securing. Additionally, as used herein, "adjacent" does not necessarily denote contact. For example, one element can be adjacent another element without being in contact with that element.

As used herein, the phrase "at least one of", when used with a list of items, means different combinations of one or more of the listed items may be used and only one of the items in the list may be needed. The item may be a particular object, thing, or category. In other words, "at least one of" means any combination of items or number of items may be used from the list, but not all of the items in the list may be required. For example, "at least one of item A, item B, and item C" may mean item A; item A and item B; item B; item A, item B, and item C; or item B and item C. In some cases, "at least one of item A, item B, and item C" may mean, for example, without limitation, two of item A, one of item B, and ten of item C; four of item B and seven of item C; or some other suitable combination.

As will be appreciated by one skilled in the art, aspects of the present invention can be embodied as a system, method, and/or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module," or "system." Furthermore, aspects of the present invention may take the form of a computer program product embodied in one or more computer readable medium(s) having program code embodied thereon.

Many of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of program code may, for instance, comprise one or more physical or logical blocks of computer instructions which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of program code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network. Where a module or portions of a module are implemented in software, the program code may be stored and/or propagated on in one or more computer readable medium(s).

The computer readable medium may be a tangible computer readable storage medium storing the program code. The computer readable storage medium may be, for example, but not limited to, an electronic, magnetic, optical, electromagnetic, infrared, holographic, micromechanical, or semiconductor system, apparatus, or device, or any suitable combination of the foregoing.

More specific examples of the computer readable storage medium may include but are not limited to a portable computer diskette, a hard disk, a random access memory (RAM), a read-only memory (ROM), an erasable programmable read-only memory (EPROM or Flash memory), a portable compact disc read-only memory (CD-ROM), a digital versatile disc (DVD), an optical storage device, a magnetic storage device, a holographic storage medium, a micromechanical storage device, or any suitable combination of the foregoing. In the context of this document, a computer readable storage medium may be any tangible medium that can contain, and/or store program code for use by and/or in connection with an instruction execution system, apparatus, or device.

The computer readable medium may also be a computer readable signal medium. A computer readable signal medium may include a propagated data signal with program code embodied therein, for example, in baseband or as part of a carrier wave. Such a propagated signal may take any of a variety of forms, including, but not limited to, electrical, electro-magnetic, magnetic, optical, or any suitable combination thereof. A computer readable signal medium may be any computer readable medium that is not a computer readable storage medium and that can communicate, propagate, or transport program code for use by or in connection with an instruction execution system, apparatus, or device. Program code embodied on a computer readable signal medium may be transmitted using any appropriate medium, including but not limited to wire-line, optical fiber, Radio Frequency (RF), or the like, or any suitable combination of the foregoing.

In one embodiment, the computer readable medium may comprise a combination of one or more computer readable storage mediums and one or more computer readable signal mediums. For example, program code may be both propagated as an electro-magnetic signal through a fiber optic cable for execution by a processor and stored on RAM storage device for execution by the processor.

Program code for carrying out operations for aspects of the present invention may be written in any combination of one or more programming languages, including an object oriented programming language such as Java, Smalltalk, C++, PHP or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The computer program product may be stored on a shared file system accessible from one or more servers. The computer program product may be executed via transactions that contain data and server processing requests that use Central Processor Unit (CPU) units on the accessed server. CPU units may be units of time such as minutes, seconds, hours on the central processor of the server. Additionally the accessed server may make requests of other servers that require CPU units. CPU units are an example that represents but one measurement of use. Other measurements of use include but are not limited to network bandwidth, memory usage, storage usage, packet transfers, complete transactions, etc.

Aspects of the embodiments may be described above with reference to schematic flowchart diagrams and/or schematic block diagrams of methods, apparatuses, systems, and computer program products according to embodiments of the invention. It will be understood that each block of the schematic flowchart diagrams and/or schematic block diagrams, and combinations of blocks in the schematic flowchart diagrams and/or schematic block diagrams, can be implemented by program code. The program code may be provided to a processor of a general purpose computer, special purpose computer, sequencer, or other programmable data processing apparatus to produce a machine, such that the instructions, which execute via the processor of the computer or other programmable data processing apparatus, create means for implementing the functions/acts specified in the schematic flowchart diagrams and/or schematic block diagrams block or blocks.

The program code may also be stored in a computer readable medium that can direct a computer, other programmable data processing apparatus, or other devices to function in a particular manner, such that the instructions stored in the computer readable medium produce an article of manufacture including instructions which implement the function/act specified in the schematic flowchart diagrams and/or schematic block diagrams block or blocks.

The program code may also be loaded onto a computer, other programmable data processing apparatus, or other devices to cause a series of operational steps to be performed on the computer, other programmable apparatus or other devices to produce a computer implemented process such that the program code which executed on the computer or other programmable apparatus provide processes for implementing the functions/acts specified in the flowchart and/or block diagram block or blocks.

The schematic flowchart diagrams and/or schematic block diagrams in the Figures illustrate the architecture, functionality, and operation of possible implementations of apparatuses, systems, methods and computer program products according to various embodiments of the present invention. In this regard, each block in the schematic flowchart diagrams and/or schematic block diagrams may represent a module, segment, or portion of code, which comprises one or more executable instructions of the program code for implementing the specified logical function(s).

It should also be noted that, in some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. Other steps and methods may be conceived that are equivalent in function, logic, or effect to one or more blocks, or portions thereof, of the illustrated Figures.

Although various arrow types and line types may be employed in the flowchart and/or block diagrams, they are understood not to limit the scope of the corresponding embodiments. Indeed, some arrows or other connectors may be used to indicate only the logical flow of the depicted embodiment. For instance, an arrow may indicate a waiting or monitoring period of unspecified duration between enumerated steps of the depicted embodiment. It will also be noted that each block of the block diagrams and/or flowchart diagrams, and combinations of blocks in the block diagrams and/or flowchart diagrams, can be implemented by special purpose hardware-based systems that perform the specified functions or acts, or combinations of special purpose hardware and program code.

The present subject matter may be embodied in other specific forms without departing from its spirit or essential characteristics. The described embodiments are to be considered in all respects only as illustrative and not restrictive. All changes which come within the meaning and range of equivalency of the claims are to be embraced within their scope.

What is claimed is:

1. An apparatus for inspecting a component, comprising:
a first feature inspector comprising at least one wave transducer configured to inspect a first feature of the component, the first feature inspector further comprising at least one displacement sensor configured to detect a displacement of the at least one wave transducer of the first feature inspector relative to the first feature of the component; and
a second feature inspector comprising at least one wave transducer configured to inspect a second feature of the component, the second feature inspector further comprising at least one displacement sensor, separate from the at least one displacement sensor of the first feature inspector, configured to detect a displacement of the at least one wave transducer of the second feature inspector relative to the second feature of the component;
wherein the at least one wave transducer of the first feature inspector is independently movable relative to the at least one wave transducer of the second feature inspector.

2. The apparatus of claim 1, wherein the first feature inspector further comprises first and second housings spaced longitudinally apart from each other along the first feature, and wherein each of the first and second housings of the first feature inspector houses at least one wave transducer.

3. The apparatus of claim 2, wherein the first feature inspector comprises a first displacement sensor movably coupled to the first housing of the first feature inspector, and a second displacement sensor movably coupled to the second housing of the first feature inspector.

4. The apparatus of claim 1, wherein the second feature inspector further comprises first and second housings spaced laterally apart from each other across the second feature, wherein each of the first and second housings of the second feature inspector houses at least one wave transducer.

5. The apparatus of claim 4, wherein the second feature inspector comprises a first displacement sensor movably coupled to the first housing of the second feature inspector, and a second displacement sensor movably coupled to the second housing of the second feature inspector.

6. The apparatus of claim 1, wherein the first feature comprises a cap, and the second feature comprises opposing webs angled with respect to the cap.

7. The apparatus of claim 1, wherein displacement of the at least one wave transducer of the first feature inspector relative to the first feature of the component corresponds with a pitch of the component, and displacement of the at least one wave transducer of the second feature inspector relative to the second feature of the component corresponds with a roll of the component.

8. The apparatus of claim 1, further comprising an optical sensor configured to detect changes in a profile of the first and second features of the component.

9. The apparatus of claim 8, wherein changes in the profile of the first and second features of the component detected by the optical sensor correspond with at least one of height and lateral changes in the profile of the first and second features of the component.

10. A system for inspecting a component, comprising:
a probe comprising (i) a first feature inspector comprising at least one wave transducer configured to inspect a first feature of the component, the first feature inspector further comprising at least one displacement sensor configured to detect a displacement of the at least one wave transducer of the first feature inspector relative to the first feature of the component; and (ii) a second feature inspector comprising at least one wave transducer configured to inspect a second feature of the component, the second feature inspector further comprising at least one displacement sensor, separate from the at least one displacement sensor of the first feature inspector, configured to detect a displacement of the at least one wave transducer of the second feature inspector relative to the second feature of the component, wherein the at least one wave transducer of the first feature inspector is independently movable relative to the at least one wave transducer of the second feature inspector;
an actuator coupled to the probe, the actuator being actuatable to adjust at least one of a linear or angular position of the probe; and
a controller operably coupled to the probe and actuator, the controller being configured to control actuation of the actuator based on at least one of the displacement of the at least one wave transducer of the first feature inspector relative to the first feature of the component or the displacement of the at least one wave transducer of the second feature inspector relative to the second feature of the component.

11. The system of claim 10, wherein the controller controls actuation of the actuator to adjust a pitch of the probe based on the displacement of the at least one wave transducer of the first feature inspector relative to the first feature of the component, and to adjust a roll of the probe based on the displacement of the at least one wave transducer of the second feature inspector relative to the second feature of the component.

12. The system of claim 10, wherein the probe further comprises at least one optical sensor configured to detect a profile of the first and second features of the component, wherein the controller is further configured to control actuation of the actuator based on changes in the profile of the first and second features of the component detected by the at least one optical sensor.

13. The system of claim 12, wherein the controller controls actuation of the actuator to adjust a lateral or height position of the probe based on changes in the profile of the first and second features of the component detected by the at least one optical sensor.

14. The system of claim 12, wherein the controller controls actuation of the actuator to adjust at least one of roll or pitch of the probe based on changes in the profile of the first and second features of the component detected by the at least one optical sensor.

15. The system of claim 12, wherein the controller controls actuation of the actuator based solely on one or more of the displacement of the at least one wave transducer of the first feature inspector relative to the first feature of the component, the displacement of the at least one wave transducer of the second feature inspector relative to the second feature of the component, and changes in the profile of the first and second features of the component detected by the at least one optical sensor.

16. The system of claim 10, wherein the controller comprises an input module and an output module, the input module being configured to receive signals from the at least one displacement sensor of the first feature inspector and the at least one displacement sensor of the second feature inspector, and the output module being configured to convert the signals received from the at least one displacement sensor of the first feature inspector and the at least one displacement sensor of the second feature inspector into actuation commands for actuating the actuator.

17. The system of claim 16, wherein:
the first feature inspector comprises at least two wave transducers and at least two displacement sensors each configured to detect a displacement of a respective one of the at least two wave transducers of the first feature inspector;
the second feature inspector comprises at least two wave transducers and at least two displacement sensors each configured to detect a displacement of a respective one of the at least two wave transducers of the second feature inspector;
the input module is configured to aggregate signals received from the at least two displacement sensors of the first feature inspector into a first aggregated signal, and aggregate signals received from the at least two displacement sensors of the second feature inspector into a second aggregated signal; and
the output module is configured to convert the first aggregated signal into a pitch command for actuating a pitch actuator of the actuator, to convert the second aggregated voltage into a roll command for actuating a roll actuator of the actuator.

18. A method for inspecting a component, comprising:
initiating inspection of a 3-dimensional structure of the component using at least one wave transducer by emitting acoustic waves into the 3-dimensional structure from the at least one wave transducer and receiving acoustic waves from the 3-dimensional structure at the at least one wave transducer;
detecting displacement of the at least one wave transducer from a desired position relative to the 3-dimensional structure; and
adjusting a position of the at least one wave transducer back to the desired position based on detected displacement of the at least one wave transducer from the desired position relative to the 3-dimensional structure.

19. The method of claim 18, further comprising determining a pitch of the 3-dimensional structure based on detected displacement of the at least one wave transducer relative to the 3-dimensional structure, and wherein adjusting the position of the at least one wave transducer comprises adjusting a pitch of the at least one wave transducer.

20. The method of claim 18, further comprising determining a roll of the 3-dimensional structure based on detected displacement of the at least one wave transducer relative to the 3-dimensional structure, and wherein adjusting the position of the at least one wave transducer comprises adjusting a roll of the at least one wave transducer.

21. The method of claim 18, further comprising detecting a profile of the 3-dimensional structure of the component using at least one optical sensor, the method further comprising adjusting a linear position of the at least one wave transducer based on a change in the detected profile of the 3-dimensional structure.

* * * * *